United States Patent [19]
Ostojic

[11] Patent Number: 5,853,379
[45] Date of Patent: Dec. 29, 1998

[54] LOWER BACK BRACE CONSTRUCTION

[76] Inventor: Stevan R. Ostojic, 6601 W. North Ave., Oak Park, Ill. 60302

[21] Appl. No.: 19,951

[22] Filed: Feb. 6, 1998

[51] Int. Cl.$^6$ ........................................................ A61F 5/00
[52] U.S. Cl. ........................................................ 602/19; 2/44
[58] Field of Search ........................... 602/19; 2/44, 45, 2/92; 128/846, 870

[56] References Cited

U.S. PATENT DOCUMENTS

| | | | |
|---|---|---|---|
| 2,913 | 1/1843 | Crain | 602/19 |
| 664,250 | 12/1900 | Fitzpatrick | 602/19 |
| 1,301,276 | 4/1919 | Kroetz | 602/19 |
| 2,828,737 | 4/1958 | Hale | 602/19 |
| 4,640,269 | 2/1987 | Goins | 602/19 |
| 4,976,257 | 12/1990 | Akin et al. | 602/19 |
| 5,007,413 | 4/1991 | Thune | 602/19 |
| 5,619,747 | 4/1997 | Boisclair et al. | 602/19 |
| 5,632,724 | 5/1997 | Lerman et al. | 602/19 |
| 5,651,764 | 7/1997 | Chiu | 602/19 |
| 5,674,187 | 10/1997 | Zepf | 602/19 |
| 5,685,831 | 11/1997 | Floyd | 602/19 |
| 5,709,648 | 1/1998 | Webb | 602/19 |

*Primary Examiner*—Linda C. M. Dvorak
*Attorney, Agent, or Firm*—Henderson & Sturm

[57] ABSTRACT

A lower back brace construction 10 including a generally cruciform shaped cover member 20 having an outer 21 and an inner 22 cover panel provided with a pair of strap arms 23 and 24 and an upper 25 and lower 26 stem portion which envelopes a brace member 40. The outer cover panel 21 is provided with an odor absorbing unit 13.

9 Claims, 1 Drawing Sheet

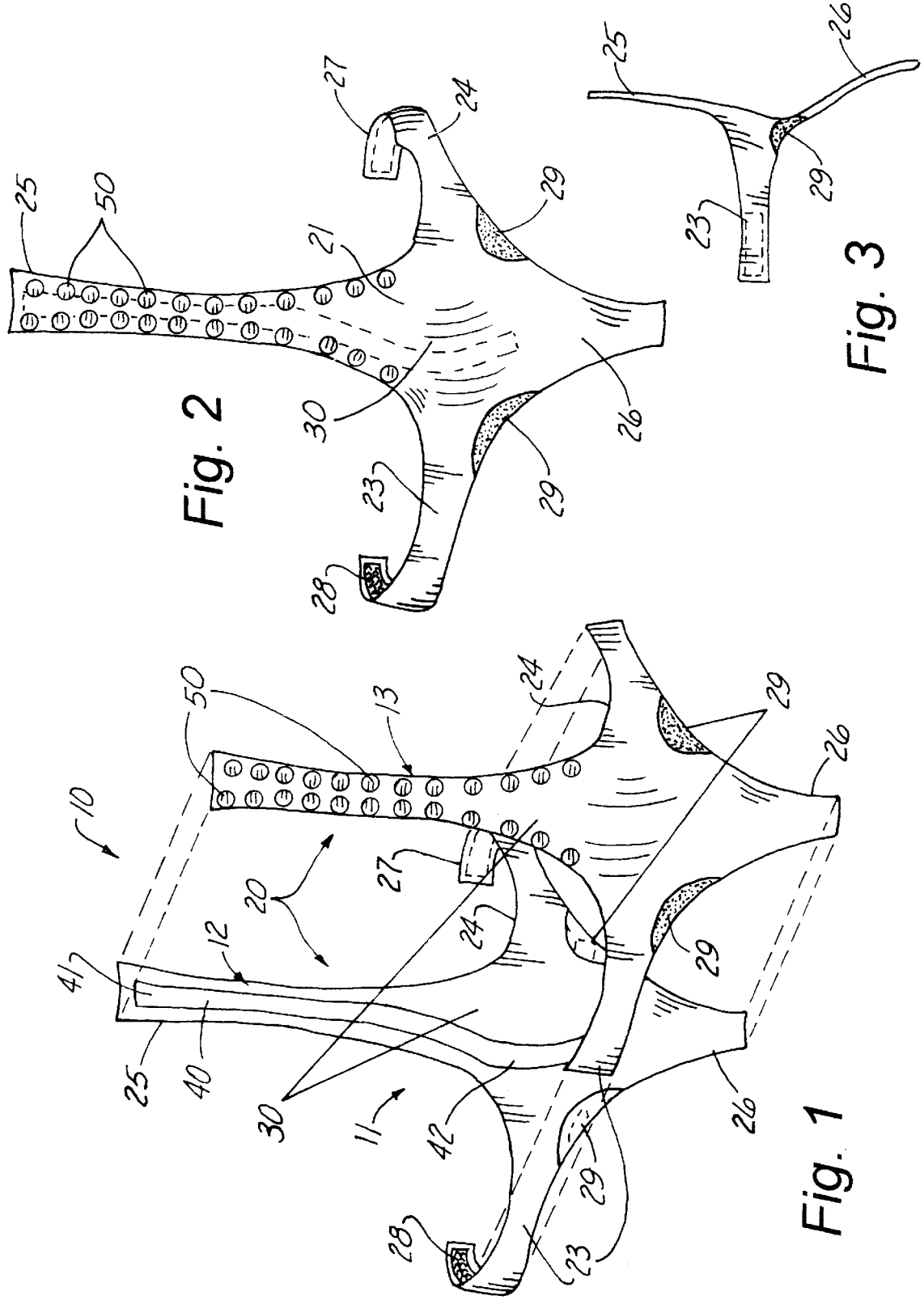

LOWER BACK BRACE CONSTRUCTION

BACKGROUND OF THE INVENTION

1. Field of the Invention

The present invention relates to the field of medical support devices in general, and in particular to a lower back brace construction.

1. Description of Related Art

As can be seen by reference to the following U.S. Pat. Nos. 5,207,636; 5,310,401; 5,363,863; and 5,447,498, the prior art is replete with myriad and diverse lower back/lumbar spine support devices.

While all of the aforementioned prior art constructions are more than adequate for the basic purpose and function for which they have been specifically designed, they are uniformly deficient with respect to their failure to provide a simple, efficient, and practical lower back brace construction that is specifically designed for physically active individuals such as athletes and construction workers, wherein their normal physical routines are physically strenuous and prone to generate inordinate amounts of perspiration.

In addition, most prior art back brace devices are rather bulky and cumbersome which severely restricts the range of motion normally required by athletes and laborers.

As a consequence of the foregoing situation, there has existed a longstanding need for a new and improved type of lower back brace construction having a relatively slim profile to provide virtually unfettered motion for the wearer and also incorporating odor absorbing elements to counteract the effects of excess perspiration, and the provision of such a construction is a stated objective of the present invention.

BRIEF SUMMARY OF THE INVENTION

Briefly stated, the lower back brace construction that forms the basis of the present invention comprises a cover unit which envelopes a brace unit and which also has an odor absorbing unit operatively associated therewith.

As will be explained in greater detail further on in the specification, the cover unit includes a generally cruciform cover member including an outer and inner cover panel wherein each cover panel has a pair of strap arms and an upper and lower stem portion which define the generally cruciform configuration.

In addition, the upper and lower stem portions of the cover member surround the brace unit which includes a contoured brace member. The outer cover panel is further provided with a plurality of activated charcoal discs that form the odor absorbing unit.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is an exploded perspective view of the lower back brace construction that forms the basis of the present invention;

FIG. 2 is a front perspective view of the back brace construction; and

FIG. 3 is a side perspective view of the construction.

DETAILED DESCRIPTION OF THE INVENTION

As can be seen by reference to the drawings, and in particularly to FIG. 1, the lower back brace construction that forms the basis of the present invention is designated generally by the reference number 10. The brace construction 10 comprises a generally cruciform cover unit 11 surrounding a contoured brace unit 12 and equipped with an odor suppressing unit 13. These units will now be described in seriatim fashion.

As can best be seen by reference to FIG. 1, the cover unit 11 comprises an elasticized cover member 20 including a pair of generally cruciform cover panels 21, 22 which represent an outer cover panel 21 and an inner cover panel 22.

In addition, each of the cover panels 21, 22 have a pair of elongated strap arms 23, 24, a relatively narrow elongated upper stem portion 25 and a tapered and truncated lower stem portion 26. The strap arms 23, 24 and the upper and lower stem portions 25, 26 are arranged in a generally cruciform configuration.

As can also be seen by reference to FIG. 1, the outboard ends of the strap arms 23 and 24 are provided with securing elements 27 and 28 which are designed to captively engage one another to releasably secure the brace construction 10 around a user's torso in a well recognized fashion.

In the preferred embodiment of the invention illustrated in FIGS. 1 and 2, one hook and loop securing element 27 is disposed on one strap arm 24 of the outer cover panel 21 and another hook and loop securing element 28 is disposed on the other strap arm 23 of the inner cover panel 22.

Still referring to FIGS. 1 and 2, it can be seen that the inboard ends of each of the strap arms 23 and 24 are provided with hip pad elements 29. In addition, the central portion 30 of each of the cover elements 21, 22 is elasticized to accommodate the brace unit 12 as will be explained presently.

As shown in FIG. 1, the brace unit 12 comprises an elongated contoured rigid brace member 40 having an elongated generally straight upper portion 41 and a generally curved lower portion 42. The brace member 40 is contoured to conform to the correct spine curvature which is illustrated in FIG. 3.

In addition, as can be seen by reference to FIGS. 1 and 2, the odor absorbing unit 13 comprises a plurality of activated charcoal discs 50 which are operatively associated with and preferably disposed on the upper stem portion 25 of the outer cover panel 21 to absorb perspiration odors both from the brace construction 10 per se and also from clothing disposed in close proximity to the brace construction 10.

By now it should be appreciated that the brace construction 10 of the invention provides a low profile brace device that does not impede the wearer's movement due to its slim profile cruciform configuration and which also includes an odor absorbing feature not found on any other brace constructions.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooded parts together, whereas, a screw employs a helical surface, in the environment of fastening wooden parts, a nail and a screw may be equivalent structures.

I claim:

1. A lower back brace construction comprising:
   a generally cruciform shaped flexible cover member including a pair of strap arms, an elongated upper stem portion and a truncated lower stem portion; and
   a brace unit including an elongated contoured brace member operatively connected to the upper and lower stem portions of said cover member.

2. The construction as in claim 1 wherein the outboard ends of the strap arms are provided with cooperating securing elements.

3. The construction as in claim 2 wherein the inboard end of the strap arms are provided with hip pad elements.

4. The construction as in claim 1 further including an odor absorbing unit.

5. The construction as in claim 4 wherein the odor absorbing unit comprises a plurality of activated charcoal disks.

6. The construction as in claim 5 wherein said plurality of charcoal disks are disposed on the upper stem portion of the cover member.

7. The construction as in claim 1 wherein said cover member includes an inner cover panel and an outer cover panel.

8. The construction as in claim 7 wherein at least a portion of the inner and outer cover panels are fabricated from an elasticized material.

9. The construction as in claim 1 wherein the central portion of the cover member is fabricated from an elasticized material.

* * * * *